United States Patent
Schmidt et al.

(10) Patent No.: US 6,894,201 B1
(45) Date of Patent: May 17, 2005

(54) PROCESS AND APPARATUS FOR THE REMOVAL OF NITROGEN COMPOUNDS FROM A FLUID STREAM

(75) Inventors: Robert J. Schmidt, Barrington, IL (US); Andrew S. Zarchy, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/741,470

(22) Filed: Dec. 19, 2003

(51) Int. Cl.[7] ............................... C07C 2/66
(52) U.S. Cl. ..................................... 585/448
(58) Field of Search .......................... 585/448

(56) References Cited

U.S. PATENT DOCUMENTS

| | | | |
|---|---|---|---|
| 2,999,861 A | 9/1961 | Fleck et al. ............... | 260/290 |
| 4,107,224 A | 8/1978 | Dwyer ................... | 260/671 R |
| 4,185,040 A | 1/1980 | Ward et al. ............... | 585/467 |
| 4,310,440 A | 1/1982 | Wilson et al. ............. | 252/435 |
| 4,440,871 A | 4/1984 | Lok et al. ................. | 502/214 |
| 4,507,438 A * | 3/1985 | Obayashi et al. .......... | 525/119 |
| 4,567,029 A | 1/1986 | Wilson et al. ............. | 423/306 |
| 4,774,377 A | 9/1988 | Barger et al. ............. | 585/323 |
| 4,846,962 A | 7/1989 | Yao ........................ | 208/301 |
| 4,891,458 A | 1/1990 | Innes et al. .............. | 585/323 |
| 5,030,786 A | 7/1991 | Shamshoum et al. ...... | 585/467 |
| 5,220,099 A | 6/1993 | Schreiner et al. ......... | 585/820 |
| 5,271,835 A | 12/1993 | Gorawara et al. ......... | 208/228 |
| 5,723,710 A | 3/1998 | Gajda et al. .............. | 585/467 |
| 5,744,686 A | 4/1998 | Gajda ...................... | 585/823 |
| 5,942,650 A | 8/1999 | Gajda ...................... | 585/448 |
| 6,019,887 A | 2/2000 | Ramirez de Agudelo ... | 208/254 R |
| 6,107,535 A | 8/2000 | Rossini et al. ........... | 585/823 |
| 6,297,417 B1 * | 10/2001 | Samson et al. ........... | 585/448 |
| 6,617,482 B1 | 9/2003 | Venkat et al. ............ | 585/448 |

FOREIGN PATENT DOCUMENTS

| | | |
|---|---|---|
| EP | 0 922 020 B1 | 5/2002 |
| WO | WO 93/00992 | 1/1993 |
| WO | WO 00/35836 | 6/2000 |
| WO | WO 01/07383 | 2/2001 |

OTHER PUBLICATIONS

Donald W. Breck, Zeolite Molecular Sieves, 1974, John Wiley & Sons, Inc., New York (pp. 45–58).

* cited by examiner

Primary Examiner—Thuan D Dang
(74) Attorney, Agent, or Firm—John G. Tolomei; James C. Paschall

(57) ABSTRACT

Disclosed is a process and apparatus for removing nitrogen compounds from an alkylation substrate such as benzene. A conventional adsorbent bed can be used to adsorb basic organic nitrogen compounds and a hot adsorbent bed of acidic molecular sieve can adsorb the weakly basic nitrogen compounds such as nitrites. Water facilitates the adsorption of the weakly basic nitrogen compounds. Running an alkylation substrate stream from a fractionation column of elevated temperature and suitable water concentration to the hot adsorbent bed may be advantageous.

24 Claims, 9 Drawing Sheets

PROCESS AND APPARATUS FOR THE REMOVAL OF NITROGEN COMPOUNDS FROM A FLUID STREAM

FIELD OF THE INVENTION

This invention relates to a process and apparatus for removing nitrogen compounds from a fluid stream. More particularly, this invention relates to the use of a selective adsorption process for removing nitrites from a hydrocarbon stream to protect an aromatic conversion catalyst.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene, or higher alkyl aromatics and in disproportionation reactions such as toluene disproportionation, xylene isomerization, or the transalkylation of polyalkylbenzenes to monoalkylbenzenes. Often the feedstock to such an aromatic conversion process will include an aromatic component or alkylation substrate, such as benzene, and a $C_2$ to $C_{20}$ olefin alkylating agent or a polyalkyl aromatic hydrocarbon transalkylating agent. In the alkylation zone, the aromatic feed stream and the olefinic feed stream are reacted over an alkylation catalyst to produce alkylated benzene such as ethylbenzene or cumene. Polyalkylated benzenes are separated from monoalkylated benzene product and recycled to a transalkylation zone and contacted with benzene over a transalkylation catalyst to yield monoalkylated benzenes and benzene.

The catalysts for such alkylation or transalkylation reactions generally comprise zeolitic molecular sieves. U.S. Pat. No. 4,891,458 discloses the presence of a catalyst comprising zeolite beta. U.S. Pat. No. 5,030,786 discloses an aromatic conversion process employing zeolite Y, zeolite omega and zeolite beta molecular sieve catalyst. U.S. Pat. No. 4,185,040 discloses the alkylation of benzene to produce ethylbenzene or cumene employing zeolites such as molecular sieves of the X, Y, L, B, ZSM-5 and Omega crystal types. U.S. Pat. No. 4,774,377, discloses an aromatic conversion process involving alkylation over a catalyst comprising a solid phosphoric acid component followed by transalkylation using aluminosilicate molecular sieve transalkylation catalysts including X, Y, ultrastable Y, L, Omega, and mordenite zeolites.

Water is often found in the aromatic feedstock to alkylation and transalkylation reactions, especially in benzene feed. Benzene feed is often water saturated, for example, when it is recycled from a styrene monomer unit. Molecular sieve catalysts employed in alkylation reactions in the vapor or the liquid phase may be sensitive to water at various levels or sulfur compounds in the feedstock. U.S. Pat. No. 4,107,224 discloses that water and hydrogen sulfide in vapor phase reactions may be tolerable if more rapid aging of the catalyst is acceptable. U.S. Pat. No. 5,030,786 disclose the dehydration of the feedstock to a water content of no more than 100 ppm, and preferably 50 ppm or less when the reaction zone is operated to maintain the reactor contents in the liquid phase. However, WO 93/00992 discloses that in the starting phase the zeolite catalyst for alkylation or transalkylation processes should have a minimum water content of more than 3.5 wt-%, related to catalyst composition. EP 0 922 020 B1 discloses uses of a solid acid to adsorb impurities from a benzene alkylation feed which is dried to contain no more than 200 ppm water at a temperature of between 130° and 300° C. to improve the lifetime of a zeolitic alkylation or transalkylation catalyst.

Other impurities present in the feedstock to an aromatic conversion reactor, particularly basic impurities such as basic organic nitrogen compounds (ONCs), neutralize the solid acids that comprise most present day aromatic alkylation catalysts. Catalyst performance and the catalyst life are adversely affected. Even very low nitrogen concentrations in the feed increase the catalyst regeneration frequency during which accumulated nitrogen compounds and coke must be combusted from the catalyst. As more active zeolite catalysts are employed in aromatic conversion reactions, the degradation of catalyst life by nitrogen impurities in the feedstock must be more carefully controlled. Processes are sought to reduce the impact of nitrogen impurities on the catalyst in the reaction zone. Basic nitrogen compounds that degrade catalyst life include indoles, pyridines, quinolines, diethanol amine (DEA), morpholines including N-formyl-morpholine (NFM) and N-methyl-pyrrolidone (NMP). NFM and NMP are used as aromatic extraction agents and DEA is a corrosion inhibitor that all often contaminate aromatic feed streams. U.S. Pat. No. 5,220,099 teaches removing indole, quinoline and pyridine impurities with zeolites and using toluene with dissolved water to desorb the impurities from the zeolites. WO 00/35836 discloses contacting an alkylated benzene with molecular sieve to remove catalyst poisons including nitrogen compounds prior to feeding it to a transalkylation reactor. WO 01/07383 discloses contacting a feed stream to an alkylation zone with a zeolite to remove organically bound nitrogen. U.S. Pat. No. 4,846,962 discloses contacting a solvent extracted oil with an amorphous silica-alumina or crystalline zeolite adsorbent to remove basic nitrogen compounds such as NMP. The adsorbent may contain up to 30 wt-% water.

U.S. Pat. No. 5,271,835 discloses the presence of polar impurities in the $C_3$ to $C_5$ product fraction from a fluid catalytic cracking unit. The impurities were found to include weakly basic ONCs such as acetonitrile. Acrylonitriles and propionitrile can also be found in hydrocarbon streams that may serve as feed to an aromatic alkylation process. These polar compounds are attracted to and poison the catalyst used in aromatics alkylation processes. U.S. Pat. No. 6,019,887 teaches using a cationic nonacidic zeolite at no more than 300° C., and U.S. Pat. No. 6,107,535 teaches using silica gel to adsorb nitriles at room temperature from a hydrocarbon stream. U.S. Pat. No. 2,999,861 teaches using an X zeolite to selectively adsorb basic ONCs over weakly basic ONCs including nitriles, nitrates and nitro compounds at −18 to 427° C. U.S. Pat. No. 5,744,686 and U.S. Pat. No. 5,942,650 teach removing water from a benzene stream containing nitriles before removing the nitriles by contacting the benzene stream with nonacidic molecular sieves at −18° to 204° C. U.S. Pat. No. 6,617,482 B1 teaches higher silica zeolites are more effective when water is present. However, only adsorption of NFM in the presence of water is demonstrated at room temperature; adsorption of nitrites is demonstrated only in the absence of water in this reference. Low concentrations of nitrites in the ranges of parts per million and parts per billion can cumulatively deactivate alkylation catalysts faster than other deactivation mechanisms such as coking.

Clay or resin guard beds are inexpensive means to adsorb ONCs from aromatic alkylation feed streams. During adsorption of organic nitrogen from alkylation feed streams, coke also forms on the adsorbents. These adsorbents become spent when all of the adsorption sites are occupied by either ONCs or coke. Spent clay and resin guard beds cannot be regenerated by combustion. Guard beds containing molecular sieves can be regenerated by combusting both ONCs and coke off of the adsorbent.

An object of the invention is to provide a guard bed that will adsorb nitrites from a hydrocarbon feed stream.

A further object of the invention is to provide a guard bed that will adsorb nitrites from a hydrocarbon feed stream to an alkylation or transalkylation zone in the presence of water.

An even further object of the invention is to provide two guard beds of different composition that will cooperatively adsorb ONCs from a hydrocarbon feed stream.

SUMMARY OF THE INVENTION

We have found that conventional adsorbents such as clay and resin materials do not sufficiently adsorb nitrites from hydrocarbon streams in the presence of water. We have further found at lower temperatures an acidic molecular sieve adsorbent preferentially adsorbs water and basic ONCs over weakly basic ONCs such as nitrites in hydrocarbon streams. However, elevated temperatures improve the capacity of acidic molecular sieve adsorbents to adsorb nitrites in the presence of water. It is hypothesized that the acidic molecular sieves serve as a catalyst at the elevated temperature to hydrolyze the nitrite to an amine or an amide. The basic amine or amide is then strongly adsorbed on the acidic molecular sieve. Hence, a conventional adsorbent bed can be used to adsorb most organic nitrogen impurities and an acidic molecular sieve can be used to adsorb remaining weakly basic organic nitrogen compounds such as nitriles. Moreover, a hydrocarbon stream from a fractionation column will have an appropriate water concentration and temperature to facilitate adsorption of nitrites by the acidic molecular sieve. The molecular sieve may be regenerated when spent. We have also discovered that the presence of water also mitigates accumulation of coke on the adsorbent, thereby prolonging the regeneration cycles.

DETAILED DESCRIPTION OF THE INVENTION

Figure 1:
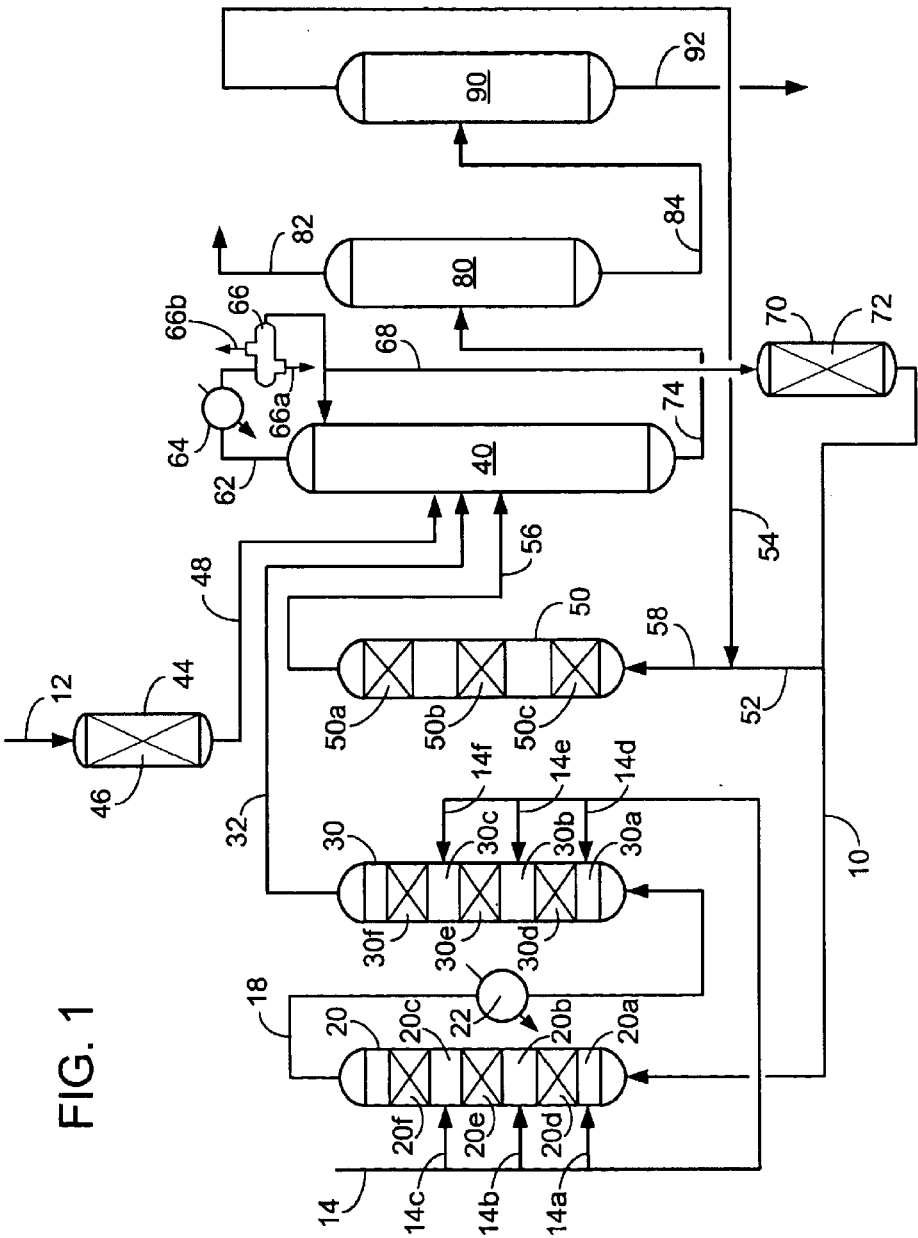
FIGS. 1–3 depict flow schemes of the present invention for the production of ethylbenzene.

The hydrocarbon feed stream of this invention is generally a liquid and may comprise from about 30 wppb to about 1 mol-% ONCs and typically 100 wppb to 100 wppm ONCs. The present invention is demonstrated to be capable of adsorbing ONCs present in concentrations in the parts per million range and we believe it can effectively nullify the effect ONC concentrations in the parts per billion range on downstream catalysts. The hydrocarbon stream may contain water up to and beyond saturation conditions. The hydrocarbon feed stream containing the ONCs and water may be an aromatic feed stream preferably including benzene and is suitably predominantly benzene. The aromatic hydrocarbon feed stream will typically include no more than 1.0 wt-% olefins when it is run through an adsorbent bed.

ONCs typically include a larger proportion of basic ONCs such as indoles, pyridines, quinolines, diethanol amine (DEA), morpholines including N-formyl-morpholine (NFM) and N-methyl-pyrrolidone (NW). ONCs also may include to a lesser proportion weakly basic nitriles, such as acetonitrile, propionitrile, acrylonitrile, and mixtures thereof. The basic ONCs are adsorbed well on conventional clay or resin adsorbent guard beds. The hydrocarbon feed stream is charged to such a conventional, impurity adsorption zone to adsorb basic ONCs and other impurities and provide a treated adsorption effluent, depleted in basic ONCs. We have found that weakly basic ONCs such as nitrites do not adsorb well on conventional resin and clay adsorbents. The nitrites get through the conventional adsorbent bed and may adversely impact downstream processing, such as an alkylation or transalkylation reaction zone.

Clay adsorbents for removing basic ONCs include clays provided by Sudchemie such as SC 630G, SC 636G and the preferred SC 626 GS. F-24 clay provided by Filtrol Corp. is also suitable. Resin adsorbents for removing basic ONCs include the Amberlyst line of resins, A-15 being preferred and available from Rohm & Haas Company, and resins such as CT-175 provided by Purolite International Limited. Other types of clay and resin adsorbents may be suitable. The clay or resin adsorber can be run at conditions sufficient to keep the aromatic stream at least partially in the liquid phase. Ambient temperature up to 38° C. (100° F.) and pressures just above atmospheric up to 206 kPa (30 psia) should be sufficient. Clays and resins capacity ranges typically between 6 and 10 wt-% amines and 1 and 2 wt-% NFM and NMP based on the weight of the adsorbent. However, under these conditions, clay and resin will preferentially adsorb water and NFM and NMP over nitrites. Hence, other measures must be taken to adsorb the nitriles.

Adsorbents of the present invention suited for the removal of weakly basic ONCs include acidic molecular sieves such as the various forms of silicoaluminophosphates, and aluminophosphates disclosed in U.S. Pat. No. 4,440,871; U.S. Pat. No. 4,310,440 and U.S. Pat. No. 4,567,029 as well as zeolitic molecular sieves. As used herein, the term "molecular sieve" is defined as a class of adsorptive desiccants which are highly crystalline in nature, with crystallographically defined microporosity or channels, distinct from materials such as gamma-alumina. Preferred types of molecular sieves within this class of crystalline adsorbents are aluminosilicate materials commonly known as zeolites. The term "zeolite" in general refers to a group of naturally occurring and synthetic hydrated metal aluminosilicates, many of which are crystalline in structure. Zeolitic molecular sieves in the calcined form may be represented by the general formula:

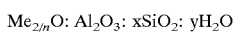

$$Me_{2/n}O: Al_2O_3: xSiO_2: yH_2O$$

where Me is a cation, x has a value from about 2 to infinity, n is the cation valence and y has a value of from about 2 to 10. Typical well-known zeolites that may be used include chabazite, also referred to as Zeolite D, clinoptilolite, erionite, faujasite, Zeolite Beta (BEA), Zeolite Omega, Zeolite X, Zeolite Y, MFI zeolite, Zeolite MCM-22 (MWW), ferrierite, mordenite, Zeolite A, and Zeolite P. Detailed descriptions of some of the above-identified zeolites may be found in D. W. Breck, ZEOLITE MOLECULAR SIEVES, John Wiley and Sons, New York, 1974.

Significant differences exist between the various synthetic and natural materials in chemical composition, crystal structure and physical properties such as X-ray powder diffraction patterns. The molecular sieves occur as agglomerates of fine crystals or are synthesized as fine powders and are preferably tableted or pelletized for large-scale adsorption uses. Pelletizing methods are known which are very satisfactory because the sorptive character of the molecular sieve, both with regard to selectivity and capacity, remains essentially unchanged. Preferred adsorbents include a Zeolite Y and a Zeolite X having an alumina or silica binder and a beta zeolite having an alumina or silica binder. Zeolite Y is the most preferred.

In an embodiment, the molecular sieve will usually be used in combination with a refractory inorganic oxide binder. Binders may include either alumina or silica with the former preferred and gamma-alumina, eta-aluminum and mixtures thereof being particularly preferred. The molecular sieve may be present in a range of from 5 to 99 wt-% of the adsorbent and the refractory inorganic oxide may be present in a range of from 1 to 95 wt-%. In an embodiment, the molecular sieve will be present in an amount of at least 50 wt-% of the adsorbent and more preferably in an amount of at least 70 wt-% of the adsorbent.

The molecular sieve in the adsorbent of the present invention is acidic. Using silicon to aluminum ratio as a gauge for acidity level, the silicon to aluminum ratio should be no more than 100 in an embodiment and no more than 25 in a further embodiment. Cations on the molecular sieve are not desirable. Hence, acid washing may be desirable to remove alkali metals such as sodium in the case of Zeolite Y and Beta Zeolite to reveal more acid sites, thereby increasing the adsorptive capacity. Aluminum migrating out of the framework into the binder should also be avoided because it reduces acidity. Incorporation of some level of cations such as alkali earth and rare earth elements into Zeolite X or Y will improve the thermal and hydrothermal stability of the framework aluminum, minimizing the amount of framework aluminum migrating out of the framework. The level of incorporation of the cations should be sufficiently low to avoid inhibiting adsorption performance. The molecular sieve adsorbent of the present invention may have the same composition as the alkylation catalyst in a downstream reactor, such as an alkylation or transalkylation unit. However, when the alkylation catalyst is more expensive than the molecular sieve adsorbent, the composition of the alkylation catalyst and the molecular sieve are preferably different.

As indicated, the presence of water adversely affects adsorption of nitrites on acidic molecular sieves at ambient temperatures. On the surface, it would appear that minimizing the amount of water in the feed to a molecular sieve guard bed would be beneficial. The water would compete with the ONCs for adsorption sites, thereby reducing the capacity of the molecular sieve for ONCs. We have confirmed at lower temperatures that water preferentially adsorbs on acidic molecular sieves over nitrites. However, we further found that in the presence of an inexcessive concentration of water, acidic molecular sieves adsorb a greater concentration of nitriles at higher temperatures. Although not wishing to be bound by any particular theory, we believe the nitrites are insufficiently basic to adsorb onto the acidic molecular sieve adsorbent. However, in the presence of water, the nitriles catalytically hydrolyze to amides or amines over the acidic molecular sieve. The basic amides or amines then adsorb onto the acidic molecular sieve.

The contaminated hydrocarbon feed stream to be purified of nitrites should be run through a nitrogen adsorption zone of acidic molecular sieve in the presence of water at an elevated temperature in an embodiment of at least about 120° C. and no more than about 300° C., in an embodiment, in the range of greater than about 125° C. and no more than about 300° C., and in a further embodiment, in the range of about 150° C. to about 200° C. The pressure in the adsorbent bed should be in the range of about 34.5 kpa to about 4136.9 kPa (gauge) (5 to 600 psig). The ONC loading on the molecular sieve adsorbent may reach from about 0.6 to about 1.0 wt-% before regeneration is needed. The ONC loading on clay adsorbent is about 1.5 to about 6.0 wt-% and the ONC loading on resin adsorbent is about twice that of clay. Because the resin or clay adsorbent has a greater adsorption capacity for ONCs and is less expensive, the impure hydrocarbon stream may be run through a conventional clay or resin guard bed to remove the basic ONCs before it is delivered to the acidic molecular sieve guard bed to remove the nitrites. However, the acidic molecular sieve guard bed will adsorb basic ONCs that survive the conventional adsorbent bed. It may be preferable to install the acidic molecular sieve adsorbent bed in downstream communication with the conventional adsorbent bed. Hence, at least a portion of the effluent from the conventional adsorbent bed should eventually feed the acidic molecular sieve adsorbent bed. Moreover, because the temperature of the effluent from the conventional adsorbent bed may be ambient, a heat exchanger may be situated in downstream communication with the conventional adsorbent bed and in upstream communication with the hot adsorbent bed to adjust the temperature suitably for the hot adsorbent bed. Hence, at least a portion of the effluent from the conventional adsorbent bed will be heated or cooled in the heat exchanger and at least a portion of the effluent from the heat exchanger will feed to the hot adsorbent bed. In an embodiment, all of the alkylation substrate stream should be denitrogenated in the hot adsorbent bed before it is fed to an alkylation and/or transalkylation reaction zone.

The water concentration of the hydrocarbon feed stream should be between about 20 wppm to about 500 wppm and preferably between 50 wppm and 150 wppm while in the molecular sieve guard bed. In an embodiment, the water concentration should be stoichiometric with respect to the conversion of nitrile to amines or amides.

We have also found that the presence of water in the molecular sieve guard bed reduces coke formation on the adsorbents at elevated temperatures. Coke accumulation on acid sites of the molecular sieve serves to block adsorption of ONCs, resulting in shorter cycles between regeneration. However, by alleviating the coke formation on the acid sites, the molecular sieve guard bed can maintain longer cycles between regeneration and maintain maximum adsorption capacity over multiple cycles of operation because each regeneration cycle will require significantly less severity.

The conventional clay or resin guard bed cannot be regenerated when spent. Instead, the spent clay or resin must be disposed. Spent molecular sieve of the present invention may be regenerated. The molecular sieve guard bed may contain one or more fixed beds of molecular sieve. As the capacity of the on-stream molecular sieve adsorption bed is reached; that is, preferably before a substantial portion of the ONCs have passed through the on-stream adsorption bed, the feed stream is directed to a stand-by molecular sieve adsorption bed in the adsorption zone. The formerly on-stream adsorption bed may then be drained by passing the contents to a fractionation zone. Otherwise, the process is stopped during regeneration of the adsorbent bed. The adsorption bed may be regenerated with a hot natural gas stream or by a carbon burn to combust the ONCs from the molecular sieve or by any other conventional method. The regenerated adsorption bed is then placed on stand-by until the on-stream adsorption bed reaches capacity.

In the selective alkylation of aromatics by an olefinic alkylation agent as catalyzed by an acidic catalyst, the olefins may contain from 2 up to at least 20 carbon atoms, and may be branched or linear olefins, either terminal or internal olefins. Thus, the specific nature of the olefin is not particularly important. What the alkylation reactions share in common is that the reactions are conducted under at least partially liquid phase conditions, a criterion readily achieved for the lower members by adjusting reaction pressures. Among the lower olefins, ethylene and propylene are the most important representatives. An olefinic feed stream comprising an alkylation agent may include ethylene and/or propylene. An olefinic feed stream comprising propylene will be at least 65 wt-% pure with the balance including a large proportion of propane, with some propylene feeds being over 99 wt-% pure. Ethylene feeds will typically be over 99 wt-% pure. Among the remaining olefins, the class of detergent range olefins is of particular interest. This class consists of linear olefins containing from 6 up through about 20 carbon atoms which have either internal or terminal unsaturation. Linear olefins containing from 8 to 16 carbon atoms are particularly useful as detergent range olefins, and those containing from 10 up to about 14 carbon atoms are especially preferred for detergent range olefins. Alkylation agents may also be provided by alkyl constituents of a polyalkylbenzene in a transalkylation reaction zone. Diethylbenzene, triethylbenzene and diisopropylbenzene are prominent examples of polyalkylbenzenes that can provide such alkylation agents.

Benzene is by far the most important representative of the alkylatable aromatic compounds which may be used as an alkylation substrate in the practice of the invention. An aromatic feed stream may comprise from about 5 to 99.9 mol-% benzene and may be a recycle stream from a styrene monomer production plant. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties containing from 1 up to about 20 carbon atoms. Another important substituents is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, and so forth; phenol, cresol, anisole, ethoxy-, propoxy-, butoxy-, pentoxy-, hexoxybenzene, and so forth.

A wide variety of catalysts can be used in the alkylation reaction zone. Suitable catalysts for use in the reaction zone will comprise any catalyst that does not suffer deleterious effects from the presence of water. Preferably, a substantial quantity of water may be tolerated or desired in the presence of the alkylation catalyst. A substantial quantity of water preferably means a water concentration in the reactants entering the alkylation zone of at least 50 wppm. The alkylation reaction zone may have a water content of as little as 20 wppm, to over 200 wppm and up to 1000 wppm or more. The preferred catalyst for use in this invention is a zeolitic catalyst. The catalyst of this invention will usually be used in combination with a refractory inorganic oxide binder. Preferred binders are alumina or silica. Suitable zeolites include zeolite beta, ZSM-5, PSH-3, MCM-22, MCM-36, MCM-49, and MCM-56. Zeolite beta is described in U.S. Pat. No. 5,723,710. Preferred alkylation catalysts are a type Y zeolite having an alumina or silica binder or a beta zeolite having an alumina or silica binder. The zeolite will be present in an amount of at least 50 wt-% of the catalyst and more preferably in an amount of at least 70 wt-% of the catalyst.

The particular conditions under which the alkylation reaction is conducted depends upon the aromatic compound and the olefin used. Since the reaction is conducted under at least partial liquid phase conditions, reaction pressure is adjusted to maintain the olefin at least partially in the liquid phase. For higher olefins the reaction may be conducted at autogenous pressure. Pressures can vary within a wide range of about 101 kPa to about 13172 kPa. As a practical matter the pressure normally is in the range between about 1379 kPa and about 6985 kPa (200 to 1000 psig) but usually is in a range between about 2069 and 4137 kPa (300 and 600 psig). But we emphasize again that pressure is not a critical variable and needs to be sufficient only to maintain at least partial liquid phase conditions. Representative alkylation temperatures include a range of between 170° and 250° C. for alkylation of benzene with ethylene and temperatures of 90° to 160° C. for the alkylation of benzene by propylene. The temperature range appropriate for alkylation of the alkylatable aromatic compounds of our invention with the olefins in the $C_2$ to $C_{20}$ range is between about 60° and about 400° C., with the most usual temperature range being between about 90° and 250° C. Reactants generally pass through the alkylation zone at a mass flow rate sufficient to yield a liquid hourly space velocity from 0.2 to 50 $hr^{-1}$ and especially from about 0.5 to 10 $hr^{-1}$.

The ratio of alkylatable aromatic compound to olefin used in the process of the invention will depend upon the degree of selective alkylation desired as well as the relative costs of the aromatic and olefinic components of the reaction mixture. For alkylation of benzene by propylene, benzene-to-olefin ratios may be as low as about 1.5 and as high as about 10.0, with a ratio of 2.0 to 8.0 being preferred. Where benzene is alkylated with ethylene, a benzene-to-olefin ratio between about 2:1 and 8:1 is preferred. For detergent range olefins of $C_6$ to $C_{20}$, a benzene-to-olefin ratio of between 5:1 up to as high as 30:1 is generally sufficient to ensure the desired alkylation selectivity, with a range between about 8:1 and about 20:1 even more highly desired.

In the production of cumene with a benzene alkylation substrate and a propylene alkylating agent, the propylene-containing stream will typically also contain propane. The propylene stream may contain from 0 to 50 wt-% propane, and typically, the propylene stream contains from 0.5 to 35 wt-% propane.

The alkylation reaction zone will often provide a wide variety of undesired by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di- and triisopropylbenzene in addition to still more condensation products. These polyalkylated aromatics contact additional aromatic substrate in a transalkylation reactor to produce additional monoalkylated product. The transalkylation reaction zone of this invention will use a zeolitic catalyst. The zeolite will be present in an amount of at least 50 wt-% of the catalyst and more preferably in an amount of at least 90 wt-% of the catalyst. In most cases the zeolitic catalyst again includes an inorganic oxide binder. The preferred inorganic oxide for use in the transalkylation catalyst is alumina with gamma-alumina, eta-aluminum and mixtures thereof being particularly preferred. The zeolite may be present in a range of from 5 to 99 wt-% of the catalyst and the refractory inorganic oxide may be present in a range of from 1 to 95 wt-%. Preferred transalkylation catalysts are a type Y zeolite having an alumina or silica binder or a beta zeolite having an alumina or silica binder.

There is no requirement that the alkylation reaction zone and the transalkylation reaction zone use the same catalyst. This process is useful for any arrangement of alkylation reaction zone and transalkylation reaction. However, it has been found that a beta zeolite or a high Y type zeolite contained in an alumina binder will perform very well when used in both the alkylation reaction zone and the transalkylation reaction zone. Therefore, in the preferred embodiment of this invention, in the cumene context, both reaction zones will use the same catalyst, beta zeolite. Whereas, in the case of ethylbenzene, the alkylation and transalkylation zones will preferably use beta zeolite and Y-type zeolite, respectively. Additionally, transalkylation reactions occur in an alkylation reaction zone and alkylation reactions occur in a transalkylation reaction zone, both zones may be referred to as alkylation zones.

It may be desirable to use a first bed of an alkylation zone or transalkylation zone that uses an acidic molecular sieve catalyst as an adsorbent zone for the removal of nitrites. In such an event, the adsorbent and the catalyst should be spaced apart. The alkylation agent should bypass the adsorption zone and be delivered to an interbed space to mix with the denitrogenated alkylation substrate exiting the adsorption zone. However, it may be preferable to contain the hot adsorption zone and the alkylation zone in separate vessels.

The transalkylation reaction can be carried out in a broad range of operating conditions that include a temperature of from 100° to 390° C. (212° to 734° F.) and pressure ranging from 101 to about 13171 kPa (14.7 to 1910 psia). Again, the pressure would generally be selected so that the reactants will remain in the liquid phase. Accordingly, preferred pressures for the transalkylation reaction zone range from 1013 to about 5066 kPa (147 to 734 psia). A liquid hourly space velocity of from 0.2 to 50 $hr^{-1}$ is desirable for the transalkylation reaction zone with LHSV of from 0.5 to 5 $hr^1$ being preferred.

The transalkylation and alkylation reaction zones may be operated and arranged in any manner that provides the desired operating temperatures and number of contacting stages. Multiple contacting stages in the alkylation zone are routinely used to provide cooling by staged addition of reactants to multiple beds of alkylation catalyst. The multiple injection of the reactants serves to cool the stages between alkylation catalyst beds and provide temperature control. The alkylation catalyst is ordinarily arranged in multiple beds to permit interbed injection of alkylating agent. The separate alkylation catalyst beds may be arranged in a single vessel or in multiple vessels. This invention can be used with a traditional parallel arrangement for the alkylation zone and the transalkylation zone where feed streams are sent independently to each reaction zone and the effluent separately recovered. Alternatively, the reaction zone may have a series flow arrangement with the effluent from the transalkylation zone cascading to the alkylation zone along with additional benzene or vice versa. In the alkylation zone, a large excess of benzene may pass through a series of alkylation catalyst beds with interstage injection of alkylating agent and any additional quantities of benzene. Alkylation reactor effluent recycle may also be used advantageously to quench individual catalyst beds for further improvement in temperature control without the need for additional consumption of fresh benzene. In the series flow arrangement a common vessel may contain a transalkylation reaction zone and one or more alkylation reaction zones. For very large units, separate vessels for the transalkylation catalyst bed and one or more of the alkylation catalyst beds may be more advantageous.

A separation zone will be used to recover alkylate product. An overhead condenser on at least one fractionation column in a separation zone may be used for the separation of water from an overhead stream and the return of a portion of the aromatic hydrocarbon condensate to the column as reflux. Removal of water from the overhead is difficult due to the high solubility of water in benzene. However, some water in the benzene stream facilitates the removal of nitrites. The overhead condenser of a benzene column may be operated to reduce the water concentration to a level of about 500 wppm. An intermediate stream from a depropanizer column may provide a benzene stream with a water concentration of 50 to 150 wppm.

DETAILED DESCRIPTION OF THE DRAWINGS

The further description of embodiments of the process and apparatus of this invention is presented with reference to the attached Figures. The Figures represent aspects of embodiments of the invention and are not intended to be a limitation on the generally broad scope of the invention as set forth in the claims. Of necessity, some miscellaneous appurtenances including valves, pumps, separators, receivers, heat exchangers, etc. have been omitted from the drawings. Only those vessels and lines necessary for a clear and complete understanding of the process and apparatus of the present invention are illustrated. In all cases, the process is a continuous process.

FIG. 1 illustrates an embodiment of this is invention for the production of ethylbenzene. A stream comprising ethylene enters the process in a line 14 and is injected into first and second alkylation reactors 20, 30, respectively. Although transalkylation reactions occur in the alkylation reactors 20, 30, alkylation reactions are predominant. Alkylation reactors are shown as upflow reactors, but downflow reactors may also be suitable. Ethylene is injected into the alkylation reactors 20, 30 in several lines 14a–f into pre-bed spaces 20a–c, 30a–c prior to entry into catalyst beds 20d–f, 30d–f. The catalyst beds 20d–f, 30d–f contain alkylation catalyst to alkylate benzene and ethylene to produce ethylbenzene. Benzene in a line 10 is fed to the first alkylation reactor 20 where it initially mixes with ethylene from the line 14a in the pre-bed space 20a and enters the catalyst bed 20d. The effluent from the catalyst bed 20d is mixed with fresh ethylene from the line 14b in the pre-bed space 20b and enters into the catalyst bed 20e. The process is repeated for the number of beds in the first alkylation reactor 20. Although three catalyst beds are shown in the alkylation reactors 20, 30, more or less may be suitable. Intermediate alkylation effluent from the first alkylation reactor 20 is transported in a line 18 to the second alkylation reactor 30. A heat exchanger 22 cools the effluent in the line 18 to a desirable alkylation temperature before it is delivered to the pre-bed space 30a. Ethylene injected into the pre-bed space 30a from the line 14d mixes with the intermediate alkylation effluent from the line 18 and enters the catalyst bed 30d. The same process is repeated for the catalyst beds 30e and 30f and the alkylation reactor effluent from the second alkylation reactor 30 is transported to a benzene column 40 in a line 32.

The alkylation reactor effluent stream may be depressured by passing through a pressure control valve which is not shown, may be heated in a heater or heat exchanger which is also not shown, or both. Additionally, more or less alkylation reactors may be suitable.

If the alkylation reactors 20, 30 and a transalkylation reactor 50 are run in parallel, as shown in FIG. 1, benzene from the line 10 is routed to the transalkylation reactor 50 through a line 52. A line 54 carries a polyethylbenzene (PEB) column overhead stream of diethylbenzene FDEB) and triethylbenzene (TEB) from the overhead of a PEB column 90 to mix with the benzene in the line 52 to provide a transalkylation feed line 58. The transalkylation reactor 50 contains three catalyst beds 50a–50c of transalkylation catalyst. More or less catalyst beds may be used in the transalkylation reactor 50. The transalkylation catalyst promotes transalkylation reactions wherein ethyl groups from the DEB and TEB are transalkylated with benzene to produce ethylbenzene. Hence, a line 56 contains a greater concentration of ethylbenzene and a lower concentration of DEB and TEB than in the transalkylation feed line 58.

As shown in FIG. 1 with the alkylation and transalkylation reactors in parallel, three different streams are fed to the benzene column 40. The alkylation reactor effluent stream in the line 32 and the transalkylation effluent stream in the line 56 feeds benzene, ethylbenzene, DEB and TEB and heavier PEBs to the benzene column 40. Fresh feed benzene in a line 12 is run through a conventional adsorbent vessel 44 containing a bed 46 of clay or resin adsorbent to adsorb impurities including basic ONCs from the benzene stream. A line 48 carries the purified fresh benzene stream to the benzene column 40. The purified benzene stream typically contains 400 to 800 wppm water. The benzene column 40 separates the feed into at least two streams. A benzene column overhead stream comprising benzene exits the benzene column through a line 62 and enters a condenser 64 where it is cooled to a temperature between about 120' and about 170° C. The condensed overhead enters a receiver 66 which includes a trap for dispensing undissolved or free water in a line 66a and light gases in a line 66b if necessary. The overhead hydrocarbon stream contaminated with ONCs including nitrites in a line 68 is transported to a hot adsorbent vessel 70 while a portion of the overhead hydrocarbon stream is refluxed to the benzene column 40. The overhead hydrocarbon stream includes about 50 to about 500 wppm of water. The hot adsorbent vessel 70 contains a hot adsorbent molecular sieve bed 72 of an acidic molecular sieve which will adsorb ONCs including nitrites at appropriate conditions. The temperature and water concentration of the overhead hydrocarbon stream in the line 68 are well suited for selective adsorption of nitriles from a hydrocarbon stream by an acidic molecular sieve. Hence, the denitrogenated benzene stream in the line 10 contains virtually no ONCs, which is no more than 30 wppb. A benzene column bottom stream comprising the product ethylbenzene and the by-products including PEBs exits the benzene column in a line 74 and enters an ethylbenzene column 80.

The ethylbenzene column 80 separates the benzene column bottom stream from the line 74 by distillation into two streams. An ethylbenzene column overhead stream comprising the product ethylbenzene exits the ethylbenzene column 80 in a line 82 and is recovered from the process. An ethylbenzene column bottom stream comprises by-product PEBs, typically including DEBs, TEBs and heavier PEBs such as butylbenzenes, dibutylbenzenes, tributylbenzenes, ethylbutylbenzenes, diethylbutylbenzenes, and diphenylethane. The ethylbenzene column bottom stream exits the ethylbenzene column 80 in a line 84, and passes to the PEB column 90.

The PEB column 90 separates the ethylbenzene column bottom stream in the line 84 into two streams. A PEB column bottom stream comprising PEBs heavier than TEB exits from the bottom of the PEB column 90 in a line 92 and is rejected from the process. The PEB column overhead stream comprising DEBs and TEBs exits the PEB column 90 in the line 54 and recycles to be mixed with the feed to the transalkylation reactor 50 in the line 52 as described previously.

The embodiment in FIG. 1 uses two adsorbent beds which cooperate to remove ONCs from the alkylation substrate feed when all of the alkylation substrate is possibly contaminated with ONCs. The bed 46 of resin or clay adsorbent removes the bulk of the ONCs while the hot adsorbent molecular sieve bed 72 adsorbs the remaining ONCs including nitriles that can poison the alkylation and transalkylation catalysts.

Figure 2:
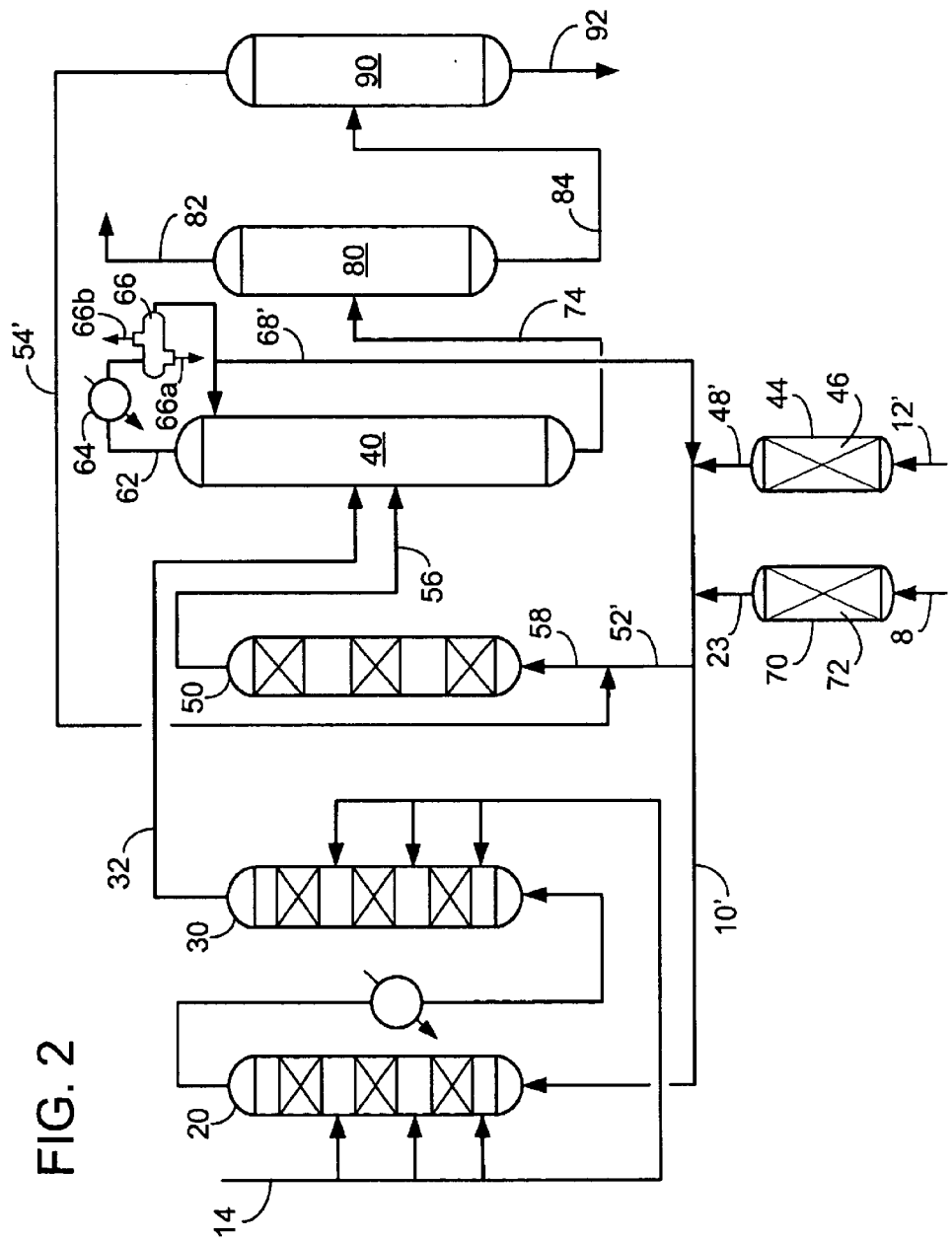

FIG. 2 shows a process and apparatus that may be advantageously used when recycle benzene from another source, such as a styrene monomer unit, is a fraction of the total benzene used to make ethylbenzene, and only the recycle benzene from the other source is possibly contaminated with nitrites. All of the reference numerals that designate an element in FIG. 2 that corresponds to a similar element in FIG. 1 but have a different configuration will be marked with a prime symbol ('). Otherwise, the same reference numeral will designate corresponding elements in FIGS. 1 and 2 that have the same configuration. Additionally, although FIG. 2 shows the alkylation reactors and the transalkylation reactors in parallel, they could be operated in series.

Fresh feed benzene in a line 12' is run through the conventional adsorbent vessel 44 containing the bed 46 of clay or resin adsorbent to adsorb impurities including ONCs from the benzene stream. No nitrites are expected in the fresh feed benzene in the line 12'. The purified benzene stream typically contains 400 to 800 wppm water. A line 48' carries the purified benzene stream to be combined with the benzene column overhead stream in a line 68'. Another source of benzene that is expected to contain nitrites is delivered in a line 8 to the hot adsorbent vessel 70. The benzene stream in the line 8 may be recycled from a styrene monomer unit and may contain between about 50 to about 800 wppm water and is typically at water saturation. The hot adsorbent vessel 70 contains the adsorbent bed 72 of an acidic molecular sieve which will adsorb ONCs including nitrites at appropriate conditions. If water concentration is below 50 wppm, water may need to be injected into the benzene stream. If the water concentration is above 500 wppm, it may be advantageous to dry the benzene stream. If the temperature of the benzene stream in the line 8 is not at least about 120° C. and preferably above 125° C. and no more than 300° C., it should be heated or cooled to the appropriate temperature. This temperature range and water concentration are well suited for selective adsorption of nitrites from a hydrocarbon stream by an acidic molecular sieve and will also adsorb basic ONCs. Hence, a denitrogenated benzene stream in a line 23 containing virtually no ONCs down to a detection level of 30 wppb is mixed with the purified benzene stream in the line 48' and the benzene column overhead stream in the line 68' to provide a nitrogen-free benzene stream in a line 10'.

The benzene stream in the line 10' is fed to the alkylation reactors 20, 30 and to the transalkylation reactor 50 through a line 52' in parallel. The benzene in the line 10' is delivered to the alkylation reactors 20, 30 and reacted with ethylene supplied by the line 14 over appropriate catalysts as explained with respect to FIG. 1. Alkylation effluent in the line 32 is delivered to the benzene column 40. DEB and TEB from the PEB overhead stream in a line 54' is mixed with the benzene stream in the line 52' to provide a transalkylation feed stream in the line 58 that is delivered to the transalkylation reactor 50. Reaction of the DEB and TEB with benzene in the reactor 50 produces an increased concentration of ethylbenzene and a decreased concentration of DEB and TEB in a transalkylation effluent stream in the line 56 relative to the transalkylation feed stream in the line 58. The transalkylation effluent stream in the line 56 is delivered to the benzene column 40.

The benzene column 40 separates the feed into at least two streams. A benzene column overhead stream comprising benzene exits the benzene column through the line 62 and enters the condenser 64 where it is cooled to between about 120° and about 170° C. The condensed overhead enters the receiver 66 which includes a trap for dispensing undissolved water in the line 66a and light gases in the line 66b if necessary. The overhead hydrocarbon stream in the line 68' containing mostly benzene is recycled to the line 10' as previously described while a portion of the overhead hydrocarbon stream is refluxed to the benzene column 40. A benzene column bottom stream comprising the product ethylbenzene and the by-products including PEBs exit the benzene column in the line 74 and enters the ethylbenzene column 80.

The ethylbenzene column 80 separates the benzene column bottom stream into an ethylbenzene column overhead stream comprising the product ethylbenzene in the line 82 and an ethylbenzene column bottom stream comprising by-product PEBs in the line 84 which is passed to the PEB column 90. The PEB column 90 separates the ethylbenzene column bottom stream into a PEB column bottom stream comprising PEBs heavier than TEB in the line 92 and the PEB column overhead stream in the line 54' recycled to the transalkylation reactor 50 as described previously.

Figure 3:
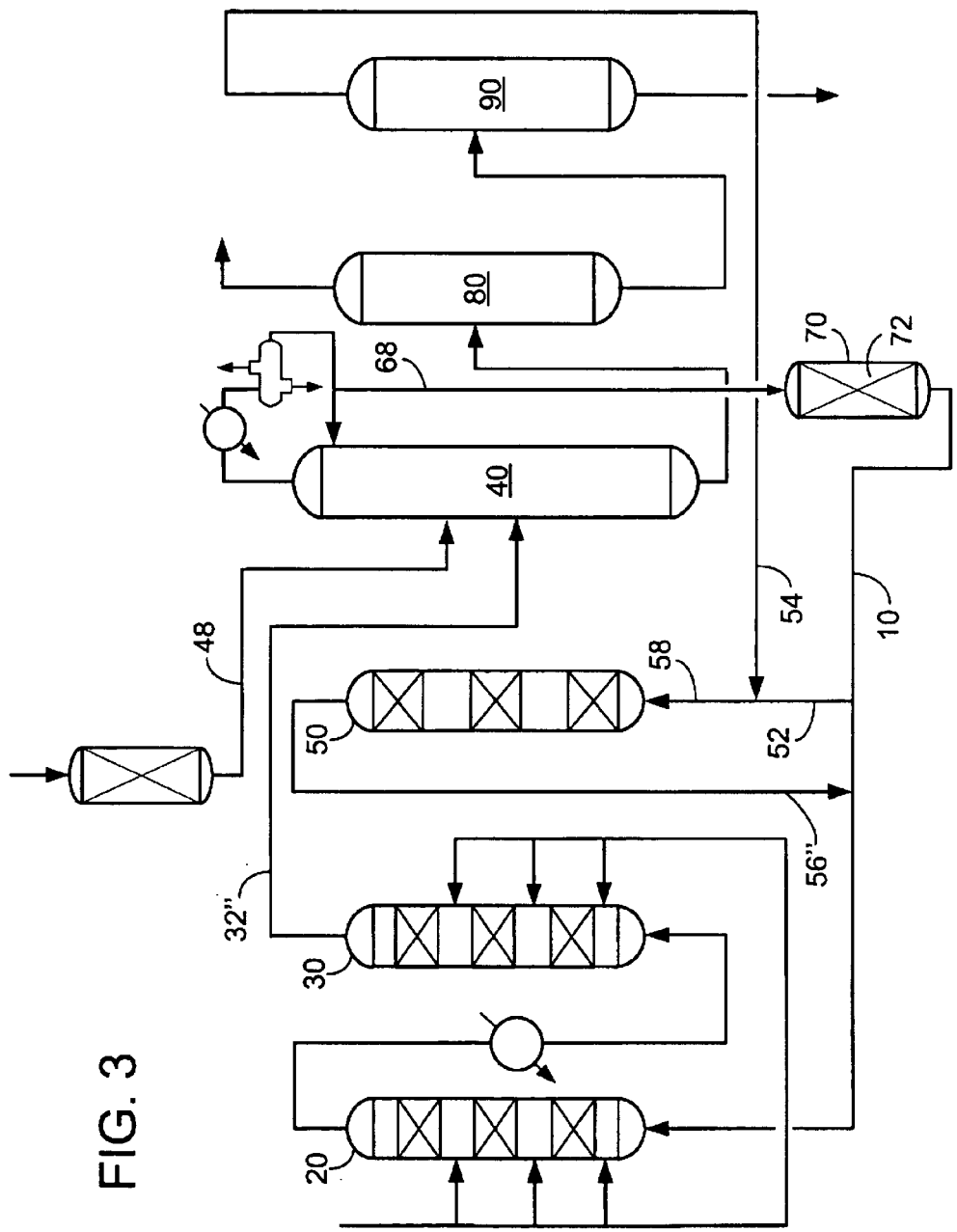

FIG. 3 shows the transalkylation reactor 50 and the alkylation reactors 20, 30 operated similarly to FIG. 1 but in series. All of the reference numerals that designate an element in FIG. 3 that corresponds to a similar element in FIG. 1 but have a different configuration will be marked with a double prime symbol ("). Otherwise, the same reference numeral will designate corresponding elements in FIGS. 1 and 3 that have the same configuration. The transalkylation reactor effluent from the transalkylation reactor 50 may be cascaded to the alkylation reactor 20 through line 56" instead of being transported to the benzene column 40. The alkylation reactor effluent in a line 32" and the purified benzene stream in the line 48 are routed to the benzene column 40. A benzene stream from the benzene column overhead stream in line 68 is denitrogenated in the hot molecular sieve adsorbent bed 72 in the hot adsorbent vessel 70. A denitrogenated benzene stream in line 10 is diverted to be transalkylation feed in line 52 and is mixed with the PEB overhead stream in the line 54 from the PEB column 90 before entering the transalkylation reactor 50 in line 58. The transalkylation effluent stream in the line 56" mixes with the remaining denitrogenated benzene stream in line 10 and enters the alkylation reactors 20, 30 as described with respect to FIG. 1.

Figure 4:
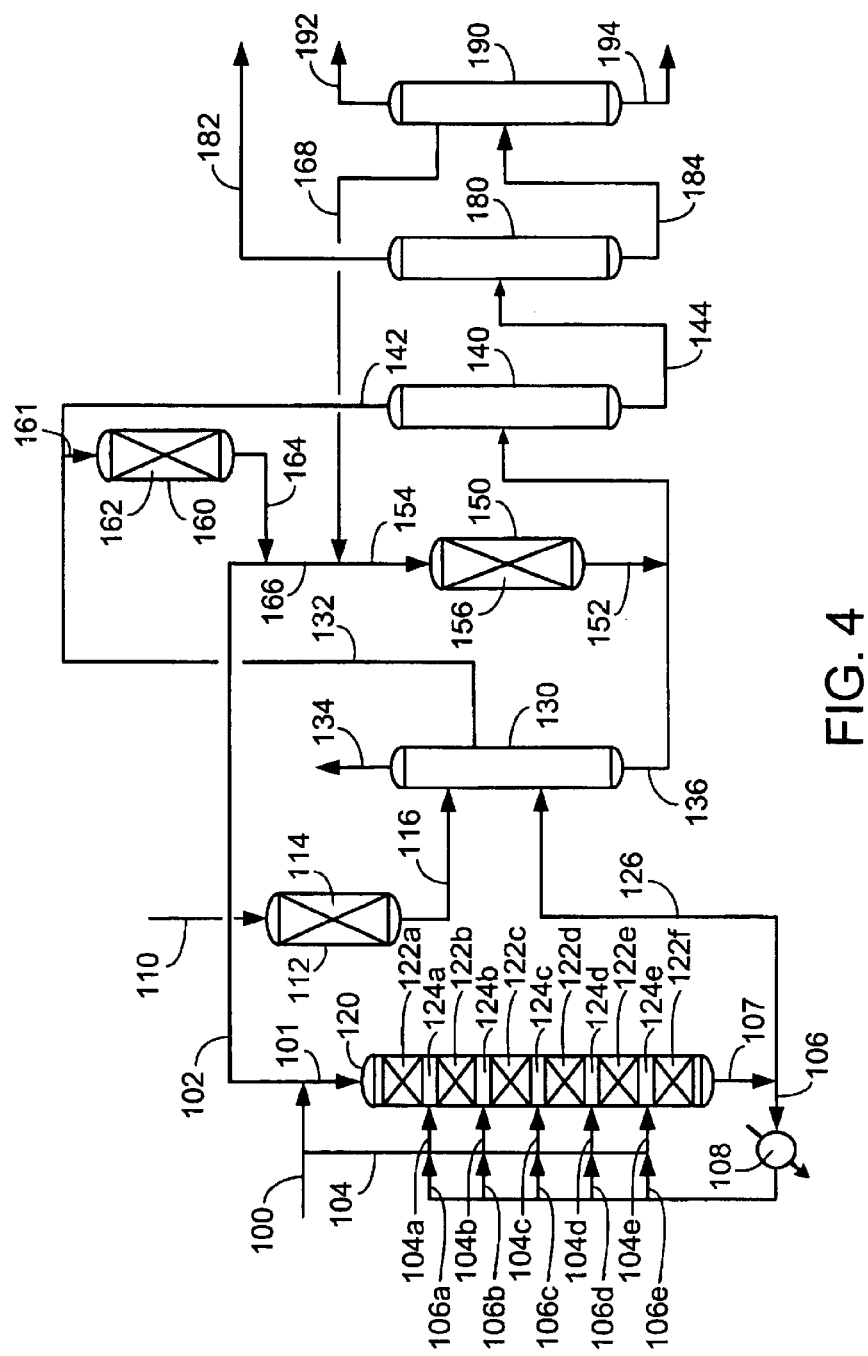
FIGS. 4–9 depict flow schemes of the present invention for the production of cumene.

FIG. 4 depicts a flow scheme for an apparatus and process for producing cumene according to the present invention. A propylene stream in a line 100 is mixed with a benzene stream in a line 102, and a line 101 introduces the mixture of benzene and propylene to a first catalyst bed 122a in an alkylation reactor 120. The alkylation reactor 120 is shown to be a downflow reactor, but an upflow reactor may be suitable. The catalyst bed 122a includes an alkylation catalyst for the alkylation of propylene and benzene to produce cumene. The effluent from the catalyst bed 122a enters an interbed space 124a. Recycled alkylation effluent from a line 106 is cooled by a heat exchanger 108 and is recycled to the alkylation reactor 120 by distribution lines 106a–e and feed inlet lines 104a–e. Propylene in a line 104 diverted from the line 100 is distributed to the feed inlet lines 104a–e in which it mixes with recycled alkylation effluent from the distribution lines 106a–e, respectively. The mixture of recycled alkylation effluent and propylene in the feed inlet lines 104a–e is delivered to the respective interbed spaces 124a–e in which it mixes with effluent from the preceding catalyst bed 122a–e, respectively, and enters the subsequent catalyst bed 122b–f, respectively. The alkylation effluent exits the last catalyst bed 122f in a line 107. A portion of the alkylation effluent is recycled by the line 106 to the alkylation reactor 120, while another portion is routed to a depropanizer column 130 in a line 126.

Fresh feed benzene in a line 110 is purified in a conventional adsorbent vessel 112 containing a bed 114 of resin or clay adsorbent to remove basic ONCs. A purified benzene stream containing about 400 to about 800 wppm water is delivered by a line 116 to the depropanizer column 130. The depropanizer column 130 provides an intermediate stream in a line 132 comprising benzene with about 50 to about 150 wppm water and a temperature of at least about 120° C. and preferably greater than 125° C. and no more than about 170° C. These properties may be regulated to prepare the benzene stream in the line 132 for adsorption of nitrites. In an embodiment, the temperature of the intermediate stream in the line 132 is a result of heat generated in the depropanizer column 130 from a reboiler (not shown) and heat taken away from the depropanizer column 130 by a condenser (not shown) which are typical equipment in a distillation column. If insufficient water is in the benzene stream because of the feed composition or other condition, water may be injected into the line 132. Additionally, although intermediate stream in the line 132 may be a side draw, a divided wall column may be used to provide a better intermediate cut. The depropanizer column 130 rejects propane and excess water in an overhead stream in a line 134. Hydrocarbons heavier than propane are withdrawn through the bottom stream in a line 136 and transported to a benzene column 140.

The benzene column 140 receives feed from the bottoms of the depropanizer column 130 in the line 136 after it is mixed with transalkylation effluent in a line 152. The benzene column 140 produces a benzene column overhead stream comprising benzene in a line 142 and a benzene column bottom stream comprising ethylbenzene and PEBs in a line 144. The overhead benzene stream in the line 142 may be provided with a water concentration of about 50 to about 150 wppm and a temperature of at least about 120° C. and preferably greater than 125° C. and no more than about 170° C. The depropanizer intermediate stream in the line 132 has similar properties, and is combined with stream 142 and delivered to a hot adsorbent vessel 160 by line 161. The hot adsorbent vessel 160 contains a bed of acidic molecular sieve adsorbent for the removal of ONCs, including nitrites from the mixed benzene stream in the line 161. The denitrogenated benzene effluent in a line 164 is delivered to both the alkylation reactor 120 by the line 102 and to a transalkylation reactor 150 by a line 166. The benzene stream in the line 166 is mixed with an intermediate stream comprising diisopropylbenzene (DIB) in a line 168 from a heavies column 190. The mixture of benzene and DIB in a line 154 are delivered to the transalkylation reactor 150. The DIB transalkylates with benzene over a transalkylation catalyst bed 156 in the transalkylation reactor 150 to produce cumene. Transalkylation effluent in the line 152 has a greater concentration of cumene and a smaller concentration of benzene and DIB than in the line 154.

The benzene column bottom stream in the line 144 is delivered to a cumene column 180. The cumene column 180 provides a cumene overhead stream comprising product cumene which is recovered in a line 182. The cumene column bottoms stream in a line 184 comprising hydrocarbons heavier than cumene is delivered to the heavies column 190. The heavies column 190 produces an intermediate stream comprising DIB in the line 168. Lighter material in the heavies overhead stream is withdrawn in a line 192 and a heavies bottom stream is withdrawn in a line 194.

Figure 5:
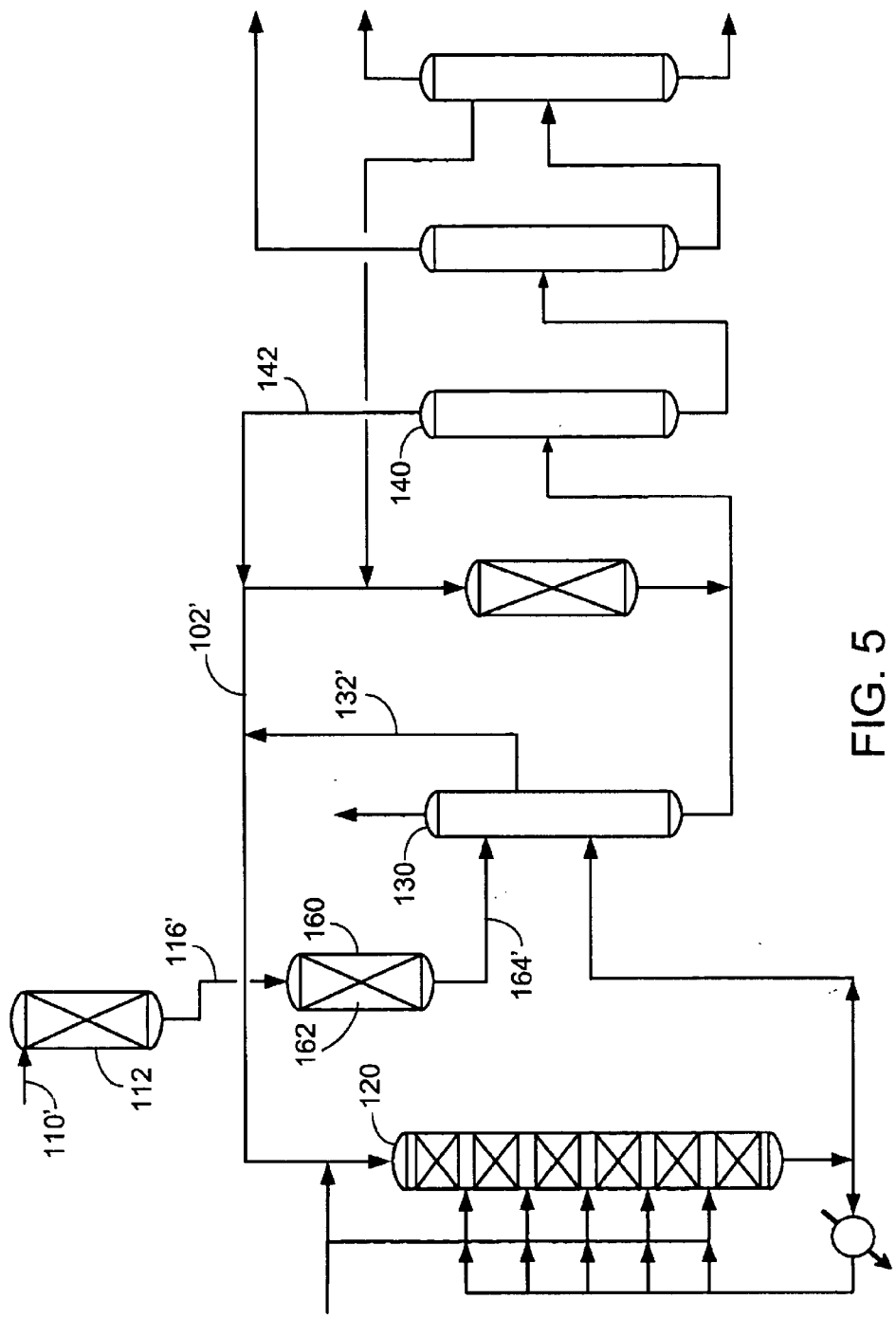

FIG. 5 shows a flow scheme similar to that in FIG. 4 except that the fresh benzene stream is purified in the conventional adsorbent vessel 112 containing the bed 114 of clay or resin adsorbent and then is denitrogenated in the hot adsorbent vessel 160 before entering the depropanizer column 130. All of the reference numerals that designate an element in FIG. 5 that corresponds to a similar element in FIG. 4 but have a different configuration will be marked with a prime symbol ('). Otherwise, the same reference numeral will designate corresponding elements in FIGS. 4 and 5 that have the same configuration. A line 10' delivers fresh feed benzene to the conventional adsorbent vessel 112, a line 116' transports purified benzene from the adsorbent vessel 112 to the hot adsorbent vessel 160 containing an acidic molecular sieve bed 162 and a line 164' feeds denitrogenated benzene to the depropanizer column 130. An intermediate stream in a line 132' from the depropanizer column 130 mixes with the benzene in a line 102' from the benzene column overhead stream in the line 142 of the benzene column 140 and is delivered to the alkylation reactor 120. Otherwise, the flow scheme of FIG. 5 operates substantially as FIG. 4.

Figure 6:
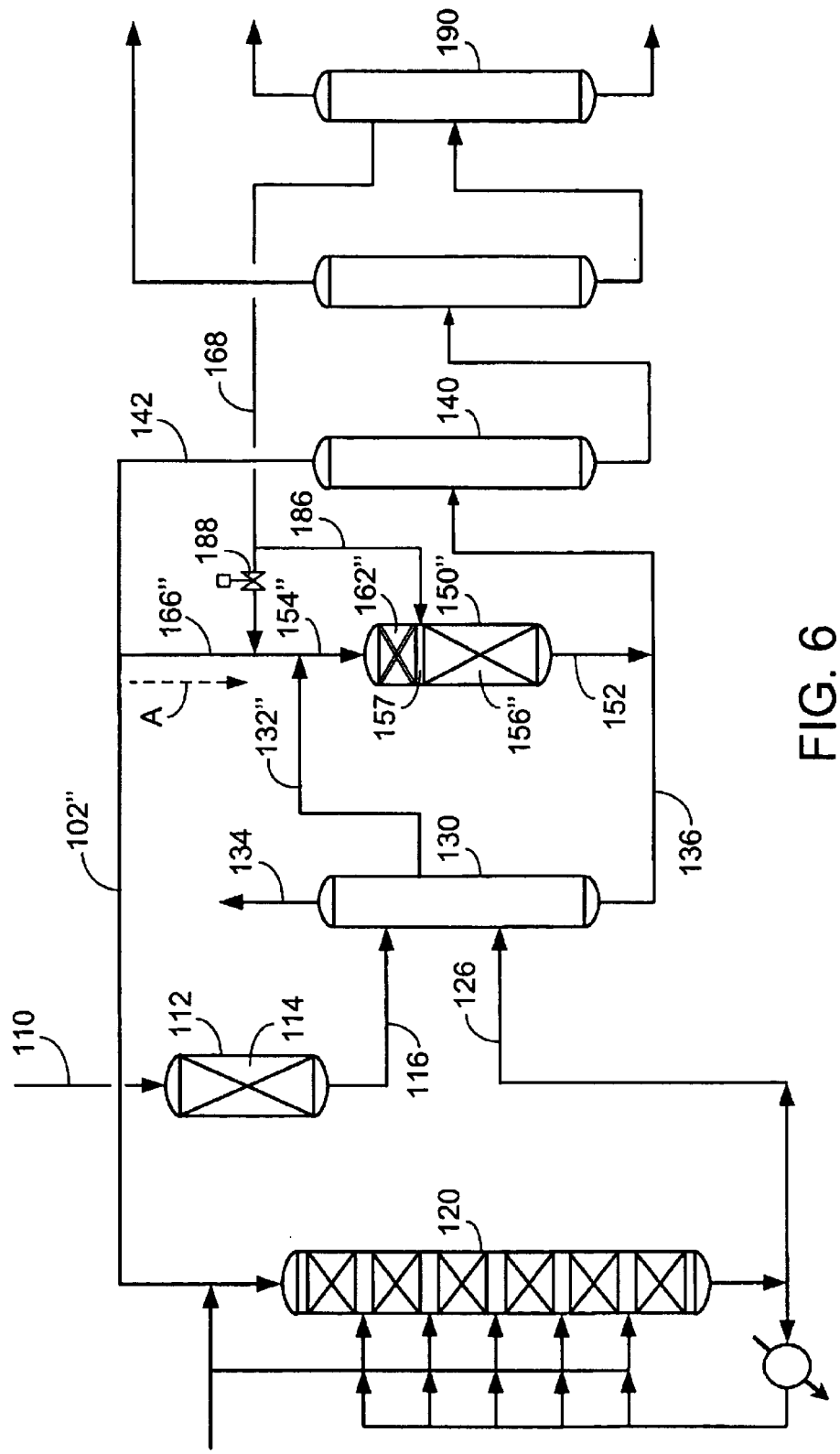

FIG. 6 shows a flow scheme similar to that in FIG. 5 but a hot adsorbent bed 162" is provided in a transalkylation reactor 150". All of the reference numerals that designate an element in FIG. 6 that corresponds to a similar element in FIG. 4 but have a different configuration will be marked with a double prime symbol ("). Otherwise, the same reference numeral will designate corresponding elements in FIGS. 4 and 6 that have the same configuration. Benzene in the line 110 is purified of basic ONCs in the conventional adsorbent vessel 112 containing the bed 114 of clay or resin adsorbent. The line 116 feeds purified benzene stream to the depropanizer column 130 along with alkylation effluent in the line 126 from the alkylation reactor 120. The depropanizer intermediate stream in a line 132" is transported and mixed with benzene from a benzene column overhead stream in the line 142 diverted through a line 166" and is fed to the transalkylation reactor 150". A control valve 188 regulates how much DIB in heavies intermediate stream in the line 168 from the heavies column 190 mixes with the diverted benzene overhead stream in the line 166" and how much bypasses a line 154" through a bypass line 186. The transalkylation reactor 150" includes the sacrificial hot adsorbent bed 162" of acidic molecular sieve catalyst for adsorbing ONCs including nitrites. Denitrogenated feed from the sacrificial hot adsorbent bed 162" mixes in an interbed space 157 with DIB from the bypass line 186 and enters a bed 156" of transalkylation catalyst. The DEB transalkylates with benzene over the transalkylation catalyst in the bed 156" to produce cumene. Transalkylation effluent in the line 152 has a greater concentration of cumene and a smaller concentration of benzene and DIB than in the line 154. Transalkylation effluent in the line 152 mixes with the depropanizer bottom stream in the line 136 and feeds the benzene column 140.

All of the nitrites in the fresh benzene stream in the line 110 that are not adsorbed in the conventional adsorbent vessel 112 and are not rejected in the depropanizer overhead stream in the line 134 will be present in the intermediate stream in the line 132". None of the nitrites should be present in the depropanizer bottom stream in the line 136. All of the nitriles from the fresh feed benzene stream in the line 110 that survive in the process will be in the line 132". The flow in the line 166" is only in the direction of an arrow "A". Hence, all of the nitriles in the line 132" will be directed to the sacrificial hot adsorbent bed 162" to remove the nitriles. No nitrites will travel up line 166" into line 102". Because no nitrites will be in heavies intermediate stream in the line 168, preferably all of the heavies intermediate stream will bypass the sacrificial hot adsorbent bed 162" through the bypass line 186.

Figure 7:
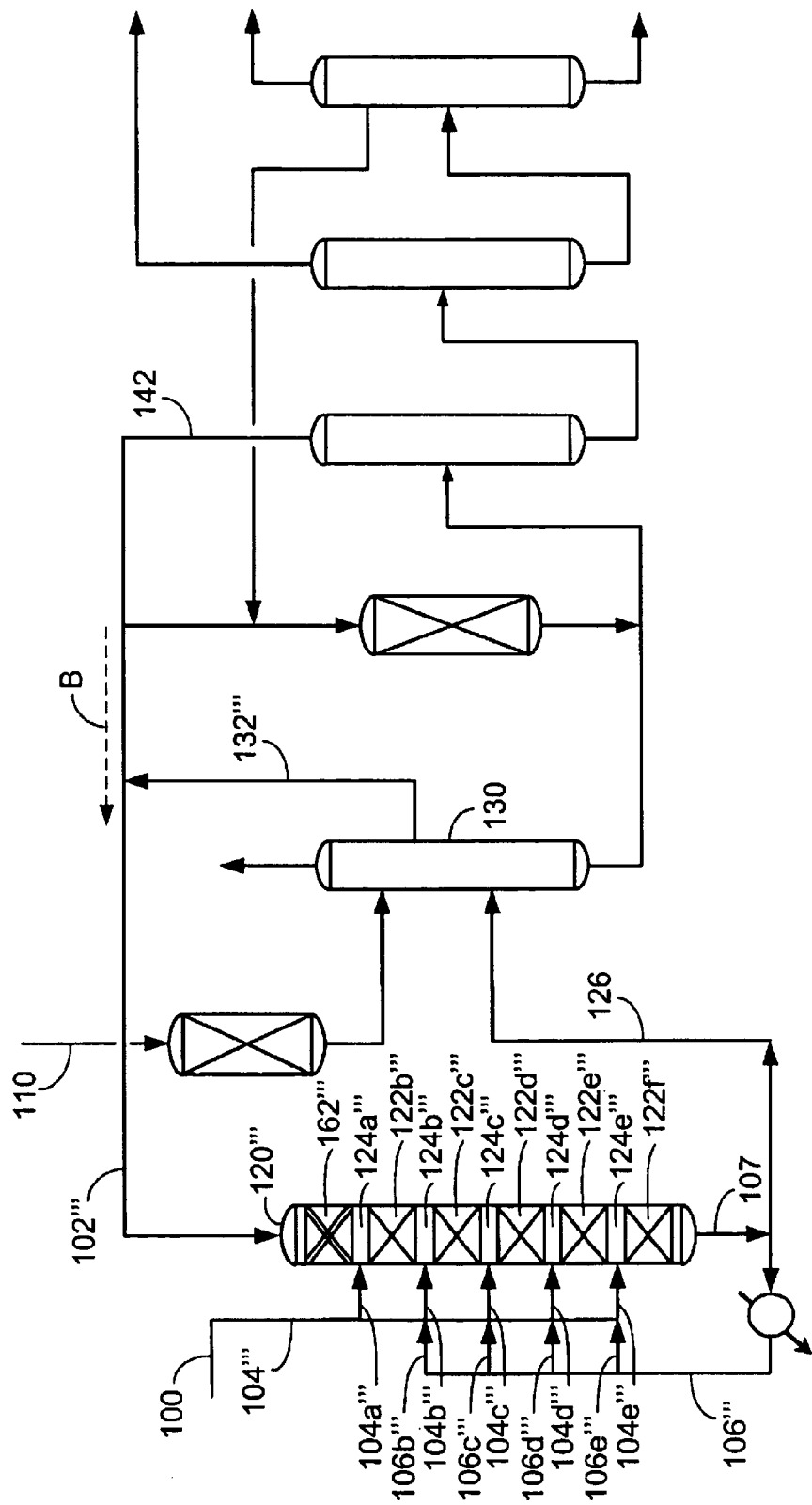

The flow scheme in FIG. 7 differs from the flow scheme in FIG. 6 in that the depropanizer intermediate stream in a line 132''' joins the benzene column overhead stream from the line 142 to form the benzene feed stream in a line 102''', and a sacrificial hot adsorbent bed 162''' is the lead bed of an alkylation reactor 120'''. All of the reference numerals that designate an element in FIG. 7 that corresponds to a similar element in FIG. 4 but have a different configuration will be marked with a triple prime symbol ('''). Otherwise, the same reference numeral will designate corresponding elements in FIGS. 4 and 7 that have the same configuration. The benzene feed stream in the line 102''' only flows in the direction of an arrow "B". As in the flow scheme of FIG. 6, all of the nitrites from the fresh feed benzene stream in the line 110 that survive in the process will be in the line 132'''. Hence, all of the nitrites in the line 132''' will be directed to the sacrificial hot adsorbent bed 162''' in the alkylation reactor 120''' to remove the nitrites.

Denitrogenated benzene effluent from the sacrificial hot adsorbent bed 162''' enters an interbed space 124a''' in which it is mixed with propylene distributed by the line 104a'''. Cooled alkylation effluent from a line 106''' is recycled to the alkylation reactor 120''' by distribution lines 106b'''–e''' to feed inlet lines 104b'''–e'''. Propylene in the line 104 is distributed to the feed inlet lines 104b'''–e''' in which it mixes with recycled alkylation effluent from the distribution lines 106b'''–e''', respectively. The mixture of recycled alkylation effluent and propylene in the feed inlet lines 104b'''–e''' is delivered to respective interbed spaces 124b'''–e''' in which it mixes with effluent from preceding catalyst bed 122b'''–e''', respectively, and enters the subsequent catalyst bed 122c'''–f''', respectively. The alkylation effluent exits the last catalyst bed 122f''' in the line 107. A portion of the alkylation effluent is recycled by the line 106''' to the alkylation reactor 120''', while another portion is routed to the depropanizer column 130 in the line 126.

Figure 8:
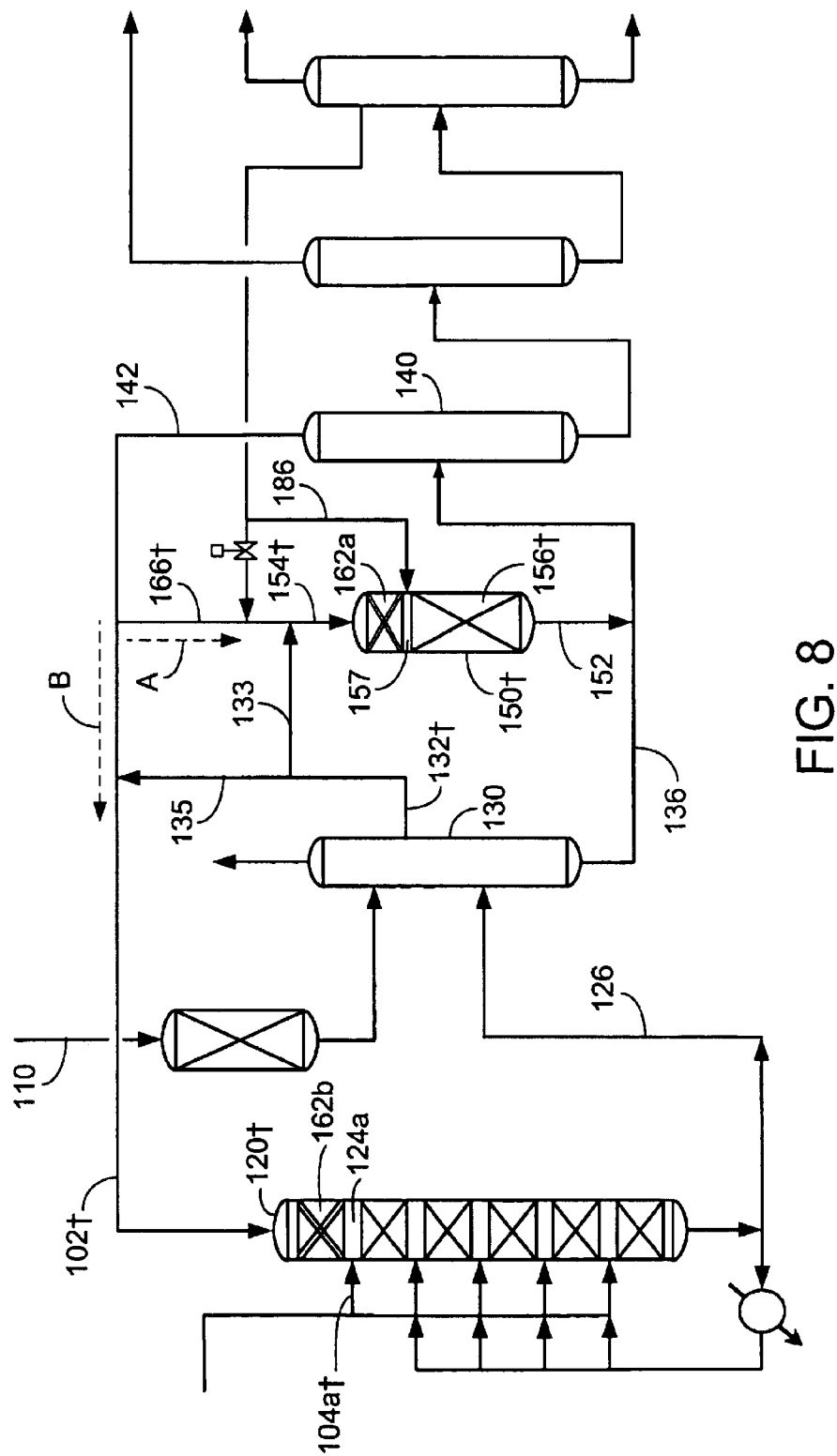

FIG. 8 depicts a flow scheme that combines the flow schemes of FIGS. 6 and 7 by using two sacrificial hot adsorbent beds. All of the reference numerals that designate an element in FIG. 8 that corresponds to a similar element in FIG. 4 but have a different configuration will be marked with a cross symbol (†). Otherwise, the same reference numeral will designate corresponding elements in FIGS. 4 and 8 that have the same configuration. One sacrificial hot adsorbent bed 162a is provided in a transalkylation reactor 150† as described with respect to FIG. 6 and a second sacrificial hot adsorbent bed 162b is provided in an alkylation reactor 120† as described with respect to FIG. 7. A depropanizer column intermediate stream in a line 132† is split into two streams. A transalkylation benzene feed stream transported in a line 133 is mixed with benzene from a benzene column overhead stream in the line 142 diverted through a line 166† and is fed through a line 154† to the transalkylation reactor 150. The sacrificial hot adsorbent bed 162a of acidic molecular sieve catalyst adsorbs ONCs including nitriles from the feed stream. Denitrogenated feed from the sacrificial hot adsorbent bed 162a mixes in the interbed space 157 with DIB from the bypass line 186 and enters a bed 156† of transalkylation catalyst. The DIB transalkylates with benzene over the transalkylation catalyst in the bed 156† to produce cumene. Transalkylation effluent in the line 152 has a greater concentration of cumene and a smaller concentration of benzene and DEB than in the line 154†. Transalkylation effluent in the line 152 mixes with the depropanizer bottom stream in the line 136 and feeds the benzene column 140.

The second stream in a line 135 derived from the depropanizer column intermediate stream in the line 132† joins the benzene column overhead stream from the line 142 to form the benzene feed stream in a line 102† and is transported to the second sacrificial hot adsorbent bed 162b leading the alkylation reactor 120†. Denitrogenated benzene effluent from the sacrificial hot adsorbent bed 162b enters the interbed space 124a in which it is mixed with propylene distributed by a line 104a†. The alkylation proceeds in the alkylation reactor 120† as explained with respect to FIG. 7. Effluent from the alkylation reactor 120† is transported to the depropanizer column 130 in the line 126. Because the diverted benzene stream in the line 166† only flows in the direction of the arrow "A", and the benzene feed stream in the line 102† only flows in the direction of the arrow "B" all of the nitriles from the fresh feed benzene stream in the line 110 that survive in the process will be in the line 132†. Hence, all of the nitriles in the line 132† will be directed to the sacrificial hot adsorbent bed 162a in the transalkylation reactor or to the sacrificial hot adsorbent bed 162b in the alkylation reactor 120† to remove all remaining ONCs, including nitriles down to 30 wppb.

Figure 9:
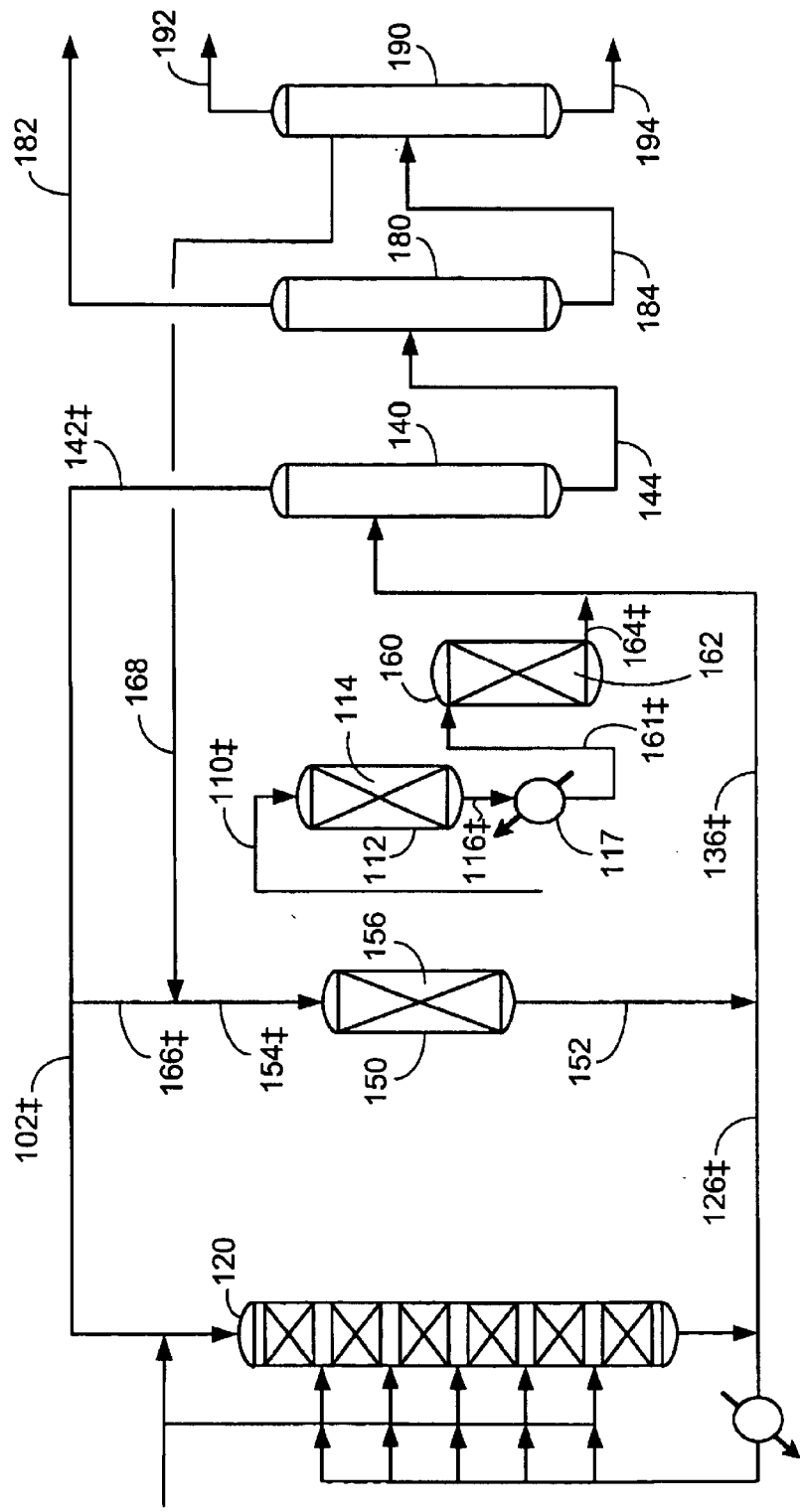

FIG. 9 depicts an additional flow scheme for making cumene according to the present invention without using a depropanizer column. All of the reference numerals that designate an element in FIG. 9 that corresponds to a similar element in FIG. 4 but have a different configuration will be marked with a double cross symbol (†). Otherwise, the same reference numeral will designate corresponding elements in FIGS. 4 and 9 that have the same configuration. Fresh feed benzene in a line 110† containing about 400 to about 800 wppm water is purified in the conventional adsorbent vessel 112 containing the bed 114 of resin or clay adsorbent to remove basic ONCs. Purified benzene stream in a line 116 is optionally heated in a heat exchanger 117 and delivered to the hot adsorbent vessel 160 by a line 161†. The hot adsorbent vessel 160 contains a bed 162 of acidic molecular sieve adsorbent for the removal of ONCs, including nitrites from the purified benzene stream in the line 161. The denitrogenated benzene effluent in a line 164† is mixed with combined alkylation and transalkylation effluent streams in a line 136† and delivered to a benzene column 140.

The benzene column 140 produces a benzene column overhead stream comprising benzene in a line 142† and a benzene column bottom stream comprising ethylbenzene and PEBs in the line 144. The overhead benzene stream in the line 142† may be provided with a water concentration of up to about 500 wppm and a temperature of at least about 120° C. and preferably greater than 125° and no more than about 170° C. A portion of the overhead benzene stream in the line 142† is diverted to the transalkylation reactor 150 by a line 166†. DIB in the heavies column intermediate stream transported by the line 168 mixes with the benzene in the line 166† to provide the transalkylation feed stream in a line 154†. The DIB transalkylates with benzene over the transalkylation catalyst bed 156 in the transalkylation reactor 150 to produce cumene. Transalkylation effluent in the line 152 has a greater concentration of cumene and a smaller concentration of benzene and DIB than in the line 154†. The benzene column overhead stream remaining in a line 102 is reacted with propylene over alkylation catalyst in the alkylation reactor 120 as described with respect to FIG. 4. Alkylation effluent in a line 126† is mixed with transalkylation effluent in the line 152 to provide combined effluent streams in the line 136†.

The benzene column bottom stream in the line 144 is delivered to the cumene column 180. The cumene column 180 provides a cumene overhead stream comprising product cumene which is recovered in the line 182. The cumene column bottoms stream in the line 184 comprising hydrocarbons heavier than cumene is delivered to the heavies column 190. The heavies column 190 produces the intermediated stream comprising DIB in the line 168. Lighter material in the heavies overhead stream is withdrawn in the line 192 and a heavies bottom stream is withdrawn in the line 194.

It should be noted that in some of the Figures, equipment such as receivers, reboilers, condensers and/or reflux lines are detailed for some equipment but not in others. However, omission of such detail in the description and Figures does not indicate that such equipment is not contemplated, but that one of ordinary skill in the art will know what equipment is necessary.

The invention will be further clarified by a consideration of the following examples, which are intended to be purely exemplary of the use of the invention.

EXAMPLES

Example I

A test was run to determine the effectiveness of an acidic molecular sieve in adsorbing acetonitrile from a benzene stream containing water at low temperatures. The adsorbent was prepared by extruding approximately 80 wt-% Y-zeolite with about 20 wt-% alumina binder. After drying the adsorbent was crushed and particles between 20 and 40 mesh were loaded into eight vessels fluidly communicated in series. Benzene feed saturated with water, which is about 500 wppm water, and loaded with 1 wppm acetonitrile was run through the eight adsorbent vessels in series at ambient temperature and pressure.

The ultimate loading in terms of adsorbed nitrogen relative to the adsorbent averaged over the eight adsorbent beds was 0.125 wt-%. The adsorbent in the first five beds had adsorbed its capacity, allowing acetonitrile through the bed, within one day and the adsorbent in beds six through eight adsorbed its capacity within two days.

Adsorbent from the beds was then rinsed with water at 50° C. for an hour. Ninety-seven percent of the nitrogen was extracted from the adsorbent. Hence, at lower temperatures water impairs the adsorption of acetonitrile and/or is adsorbed preferentially to acetonitrile.

Example II

A series of test were conducted to compare the adsorption performance of clay, resin and molecular sieve adsorbents for acetonitrile, NMP and NFM. The adsorbents were loaded into eight vessels fluidly communicated in series. Toluene feed saturated with water, which is about 500 wppm water, and target loaded with 1 wppm each of acetonitrile, NFM and NMP was run through the eight adsorbent vessels in series at ambient temperature and pressure. A toluene feed for one experiment was without water. The Y zeolite was prepared by extruding approximately 80 wt-% Y-zeolite with about 20 wt-% alumina binder.

Table I compares the time it takes for organic nitrogen impurities to break through the selected adsorbent beds.

TABLE I

| Adsorbent | Clay (SC-626GS) | Resin (A-15) | Y Zeolite | Y Zeolite |
|---|---|---|---|---|
| Feed | Water Saturated | Water Saturated | Water Saturated | Dry |
| ACN breakthrough in initial bed (days) | immediate | 0.9 | immediate | 0.1 |
| ACN breakthrough in eighth bed (days) | 1.6 | 0.8 | 0.1 | 5.0 |
| NMP breakthrough in initial bed (days) | 6.9 | immediate | 0.1 | 0.1 |
| NMP breakthrough in eighth bed (days) | 30.6 | >15 | >7 | >8 |
| NFM breakthrough in initial bed (days) | 6.9 | immediate | 0.1 | 0.1 |
| NFM breakthrough in eighth bed (days) | >30 | 15.0 | 6.7 | 7.0 |
| Nitrogen on adsorbent (wt-%) | 1.3 | 1.4 | 0.9 | 0.8 |

Table I indicates that none of the beds under these conditions were effective to adsorb acetonitrile for a prolonged period. The Y zeolite may be effective to adequately adsorb acetonitrile from dry feed if a sufficiently large bed is utilized because break through in the initial bed was early, but reasonably prolonged in the eighth bed. Clay adsorbent seemed to be the most effective with NMP and NFM. Resin seemed to adequately adsorb NFM and NMP only if a sufficiently large bed of resin adsorbent is utilized because breakthrough of the initial bed was immediate but prolonged in the eighth bed.

Example III

A series of tests were conducted to evaluate the removal of acetonitrile (ACN) from benzene by contacting it with an adsorbent prepared by extruding approximately 80 wt-% Y-zeolite with about 20 wt-% alumina binder. The adsorbent had an ABD of 0.625 g/cc. For all tests, the adsorbent was dried at 120° C. for 2 hours prior to loading 25 grams of the adsorbent into a vessel. The tests were run at 24° C. and 150° C. operating temperatures and with varying amounts of water in the feed benzene.

Feedstock for the tests was prepared by spiking the benzene stream with ACN to give a target of approximately 20 wppm nitrogen. The starting benzene feed was dried before it was spiked with the ACN. In two of the tests, the benzene feed was spiked with water to determine the effect of water on the nitrogen adsorption. Results of spent adsorbent analysis for four tests are summarized in Table II.

TABLE II

| Test No. | Temperature (° C.) | Nominal Water Content (wppm) | Spent Adsorbent Average Nitrogen Content (wt-%) |
|---|---|---|---|
| 1 | 25 | 0 | 0.86 |
| 2 | 150 | 0 | 0.49 |
| 3 | 150 | 50 | 1.07 |
| 4 | 150 | 500 | 0.83 |

From Table II, it is evident that at elevated temperatures, in the range of 150° C., the addition of water to the feed improves the nitrogen capacity of the adsorbent. The test with 50 wppm water at 150° C. shows approximately 25% greater nitrogen capacity than the test at ambient temperature with no water in the benzene feed.

Example IV

The adsorbent from Test Nos. 2 and 3 in Example 1 were subjected to thermal gravimetric analysis (TGA) to determine the extent of coke accumulation on the adsorbents. The weight percent of coke deposited on the adsorbents and the temperature required to combust the coke from the adsorbents were estimated and shown in Table III.

TABLE III

| Test No. | Est. Coke Weight (wt-%) | Est. Combustion Temperature (° C.) |
|---|---|---|
| 2 | 8 | >400 |
| 3 | <1 | <400 |

Based on the TGA data, temperatures in excess of 400° C. were required to combust coke from the adsorbent from Test No. 2. Additionally, the coke level of adsorbent sample from Test No. 2, conducted at 150° C. and no water, is approximately 8 wt-%. Conversely, the adsorbent from Test No. 3 did not show a significant weight loss as the temperature increased above 400° C. It was estimated that the coke level of this adsorbent sample of Test No. 3, from the experiment conducted at 150° C. and 50 wppm water, is less than 1 wt-%. Therefore, addition of water has decreased the coke formation on the adsorbent by more than 85%. Regeneration of adsorbent will be less frequent when water is present during adsorption of nitrites at elevate temperatures.

What is claimed is:

1. A process for alkylating an alkylation substrate with an alkylation agent, said process comprising:
   passing an alkylation substrate feed stream comprising an alkylation substrate and a nitrogen-containing compound to a separation zone;
   recovering from the separation zone a contaminated substrate stream comprising the alkylation substrate and the nitrogen-containing compound;
   passing at least a portion of a stream containing the alkylation substrate to an impurity adsorption zone containing an adsorbent selective for the adsorption of impurities comprising basic organic nitrogen compounds;
   passing at least a portion of the contaminated substrate stream to a nitrogen adsorption zone containing an adsorbent selective for the adsorption of the nitrogen compound, and recovering from the adsorption zone a denitrogenated substrate stream comprising the alkylation substrate and having a concentration of the nitrogen-containing compound that is less than the concentration of the nitrogen-containing compound in the contaminated substrate stream; and passing an alkylation agent and at least a portion of the denitrogenated substrate stream comprising the alkylation substrate to an alkylation reaction zone separate from the nitrogen adsorption zone, alkylating the alkylation substrate with the alkylation agent over an alkylation catalyst to produce alkylate, and recovering from the alkylation reaction zone the reaction effluent stream comprising the alkylate.

2. The process of claim 1 wherein said alkylation substrate feed stream includes water.

3. The process of claim 1 wherein said contaminated substrate stream includes water.

4. The process of claim 1 further including passing at least a portion of a reaction effluent stream to the separation zone.

5. The process of claim 1 wherein said alkylation catalyst and said adsorbent in said nitrogen adsorption zone are different.

6. The process of claim 2 wherein the contaminated substrate stream includes between 50 and 150 wppm water.

7. The process of claim 1 wherein said contaminated substrate stream is heated or cooled before entering the nitrogen adsorption zone.

8. The process of claim 1 wherein the nitrogen adsorption zone includes no more than 1.0 wt-% alkylation agent.

9. The process of claim 1 wherein the adsorbent selective for the adsorption of impurities is a clay or a resin.

10. The process of claim 1 wherein the adsorbent selective for the adsorption of the nitrogen compound is an acidic molecular sieve.

11. The process of claim 9 wherein the adsorbent comprises a material selected from the group of zeolite beta and zeolite Y.

12. The process of claim 1 wherein the nitrogen-containing compound comprises a nitrile.

13. The process of claim 1 wherein the alkylation substrate comprises benzene and the alkylation agent is either propylene or ethylene.

14. The process of claim 1 wherein the contaminated substrate stream is an intermediate stream from the separation zone.

15. A process for alkylating an alkylation substrate with an alkylation agent, said process comprising:

passing a first alkylation substrate feed stream comprising an alkylation substrate and impurities to an impurity adsorption zone containing a purifying adsorbent comprising clay or resin selective for the adsorption of impurities and recovering from the impurity adsorption zone a purified alkylation substrate feed stream comprising the alkylation substrate and having a concentration of impurities that is less than the concentration of impurities in the first alkylation substrate feed stream;

passing a second alkylation substrate feed stream comprising an alkylation substrate, at least 20 wppm water and a nitrile compound to a nitrogen adsorption zone containing a denitrogenating adsorbent selective for the adsorption of nitriles, and recovering from the adsorption zone a denitrogenated alkylation substrate stream comprising the alkylation substrate and having a concentration of the nitrile compound that is less than the concentration of the ntrile compound in the second alkylation substrate feed stream, the denitrogenating adsorbent being different from the purifying adsorbent; and passing an alkylation agent and at least a portion of the purified substrate stream and at least a portion of the denitrogenated alkylation substrate stream comprising the alkylation substrate to an alkylation reaction zone containing an alkylation catalyst, said impurity adsorption zone and said nitrogen adsorption zone being spaced from said alkylation reaction zone, alkylating the alkylation substrate with the alkylation agent to produce alkylate, and recovering from the alkylation reaction zone the reaction effluent stream comprising the alkylate.

16. The process of claim 15 wherein the alkylation catalyst is different from the denitrogenating adsorbent.

17. The process of claim 15 wherein the alkylation reaction zone and the nitrogen adsorption zone are in two separate vessels.

18. The process of claim 15 wherein no more than 1 wt-% alkylation agent is present in the nitrogen adsorption zone.

19. The process of claim 15 wherein the denitrogenating adsorbent is a molecular sieve and the purifying adsorbent is a resin.

20. The process of claim 15 wherein that the denitrogenating adsorption zone operates at adsorption conditions comprising a temperature of greater than 125° C.

21. The process of claim 15 wherein the denitrogenating adsorbent is a molecular sieve.

22. The process of claim 15 wherein the denitrogenating adsorbent is a molecular sieve and the purifying adsorbent is a clay.

23. The process of claim 15 wherein the denitrogenated alkylation substrate feed stream contains at least a portion of the purified alkylation substrate feed stream.

24. A process for alkylating an alkylation substrate with an alkylation agent, said process comprising:

passing an alkylation substrate feed stream comprising an alkylation substrate and impurities to an impurity adsorption zone containing a purifying adsorbent comprising clay or resin selective for the adsorption of impurities and recovering from the impurity adsorption zone a purified alkylation substrate feed stream comprising the alkylation substrate and having a concentration of impurities that is less than the concentration of impurities in the alkylation substrate feed stream;

passing at least a portion of the purified alkylation substrate feed stream comprising at least 20 wppm water and a nitrile compound to a nitrogen adsorption zone containing a denitrogenating adsorbent selective for the adsorption of nitriles, and recovering from the adsorption zone a denitrogenated alkylation substrate stream comprising the alkylation substrate and having a concentration of the nitrile compound that is less than the concentration of the nitrile compound in the purified alkylation substrate feed stream, the denitrogenating adsorbent being different from the purifying adsorbent; and passing an alkylation agent and at least a portion of the denitrogenated alkylation substrate stream comprising the alkylation substrate to an alkylation reaction zone containing an alkylation catalyst, said nitrogen adsorption zone being spaced from said alkylation reaction zone, alkylating the alkylation substrate with the alkylation agent to produce alkylate, and recovering from the alkylation reaction zone the reaction effluent stream comprising the alkylate.

* * * * *